United States Patent [19]

Rokos

[11] Patent Number: 5,698,408
[45] Date of Patent: Dec. 16, 1997

[54] PTERIN DERIVATIVES THE PREPARATION THEREOF AND THE USE THEREOF

[75] Inventor: Hartmut Rokos, Berlin, Germany

[73] Assignee: B.R.A.H.M.S. Diagnostica GmbH, Berlin, Germany

[21] Appl. No.: 525,553

[22] PCT Filed: Mar. 3, 1994

[86] PCT No.: PCT/EP94/00632

§ 371 Date: Nov. 2, 1995

§ 102(e) Date: Nov. 2, 1995

[87] PCT Pub. No.: WO94/21636

PCT Pub. Date: Sep. 29, 1994

[30] Foreign Application Priority Data

Mar. 19, 1993 [DE] Germany ............ P 43 08 739.6

[51] Int. Cl.$^6$ .............. G01N 33/535; G01N 33/547; C07D 475/04; C07K 2/00
[52] U.S. Cl. ............. 435/7.9; 435/7.92; 436/518; 544/258; 530/405
[58] Field of Search ............ 435/7.1, 7.9, 7.92; 436/501, 505, 544, 518; 530/403, 405; 544/258

[56] References Cited

FOREIGN PATENT DOCUMENTS

| 0 370 960 | 8/1989 | European Pat. Off. |
|---|---|---|
| 30 12 92 | 3/1993 | Germany . |
| 3090081 | 4/1991 | Japan . |
| 2 056 459 | 7/1980 | United Kingdom . |

OTHER PUBLICATIONS

Rautenberg et al, "New Competitive Enzyme Immunoassay for the Determination of Neopterin in Human Serum" (in German), Klin. Lab. 39, 503–510(1993).
Sugimoto et al., "An Enzyme Immunoassay for Neopterin and Biopterin Using a Microtitre Plate Linked with N2–(3–Aminopropyl) Derivatives of Pteridines", Pteridines 2, 141–146 (1990).

Primary Examiner—Marian C. Knode
Assistant Examiner—Donna C. Wortman
Attorney, Agent, or Firm—Jacobson, Price, Holman & Stern, PLLC

[57] ABSTRACT

Pterin derivatives having the general formula I wherein $R_1$ represents a group —(CHOH)$_2$—CH$_3$ or —(CHOH)$_2$—CH$_2$OH, $R_2$ and $R_3$ are not the same and represent either hydrogen or the group —(CH$_2$)$_3$CONH(CH$_2$)$_4$—NH—R$_4$, wherein $R_4$ represents hydrogen or a usual label group for immunoassays or usual coating/support materials for solid phase immunoassays or immunogenic groups for the preparation of antibodies are useful for the preparation of sensitive immunoassays for the determination of neopterin and biopterin.

5 Claims, No Drawings

PTERIN DERIVATIVES THE PREPARATION THEREOF AND THE USE THEREOF

This application is a 371 of PCT/EP94/00632 filed Mar. 3, 1994, published as WO94/21636 Sep. 29, 1994.

Neopterin and dihydroneopterin are predominantly produced and secreted by monocytes/macrophages of primates (and to a lesser degree by lower mammals) after activation by interferons and lipopolysaccharides. Increased neopterin levels can be determined in body fluids of patients with diseases which involve activation of the cellular immune system.

The determination of neopterin levels has proven to be diagnostically useful, e.g. prognostically for transplant rejection and HIV infection or in screening for otherwise unrecognized infectious diseases of blood donors in order to increase the safety of blood transfusions. The measurement of neopterin may be accomplished by various methods, e.g. by high pressure liquid chromatography (HPLC) with fluorescence detection, radioimmunoassay, thin layer chromatography, etc. Dihydroneopterin can be determined as neopterin after an oxidation step (with iodine or manganese dioxide) at low pH using known procedures or alternatively as dihydroneopterin by HPLC with electrochemical detection.

Tetrahydrobiopterin ($BH_4$) is the cofactor of essential enzymes, e.g. the aromatic amino acid hydroxylases (synthesis of the neurotransmitters dopamine and hydroxytryptamine) and the nitric oxide synthetases. Therefore, its determination could be valuable. Biopterin itself is not present in body fluids; however, it is quantitatively obtained from $BH_4$ by acidic oxidation and can be determined by various methods, like neopterin above.

Non-radioactive immunoassays have also been described in the literature, however hitherto no enzyme immunoassay for the determination of neopterin in serum which is easy to perform (in comparison to HPLC) and which provides correct results has been introduced into the market.

A radioimmunoassay for the determination of pterins has been described in DE-A-30 25 226, wherein the spacer group between the amino group in position 2 and the label group is a straight-chain or branched alkylene group having from 1 to 6 carbon atoms. These immunoassays are not sufficiently sensitive to be suitable for performing routine determinations of neopterin or biopterin with reliable results.

The immunoassays according to EP-A-0 370 960 comprising a hexanoic acid group as the spacer group, also lead to unsatisfactory results.

Thus, it is the object of the present invention to provide substances in order to prepare substantially more reliable immunoassays, esp. non-radioactive assays to measure neopterin levels in body fluids. Extensive investigations resulted in the unexpected finding that such immunoassays can be developed, if the spacer group between the pterin ring and the label group is a ω-aminobutyl-carboxamidopropyl group [$H_2N$—$(CH_2)_4$—NH—CO—$(CH_2)_3$—], which is linked through the propyl group to the amino group at $C^2$ ("$N^2$") or to the $N^3$ of neopterin or biopterin.

Accordingly, under a first aspect the present invention relates to pterin derivatives having the general formula I Neopterin and Biopterin have the formula $$H\underset{H_2N}{\overset{}{\underset{N_3}{\|}}}\overset{O}{\underset{N_1}{\|}}\overset{}{\underset{N_8}{\|}}\overset{N_5}{\underset{}{\|}}CHOH-CHOH-CH_2X$$

The nomenclature used herein has the following meanings:
$N^3$: nitrogen at position 3 of the pterin ring
$N^2$: nitrogen attached to the carbon at position 2 of the pterin ring $$R_2\underset{R_3-HN}{\overset{}{\underset{N}{\|}}}\overset{O}{\underset{N}{\|}}\overset{}{\underset{N}{\|}}\overset{N}{\underset{}{\|}}R_1 \quad\quad I$$

wherein $R_1$ represents a group —$(CHOH)_2$—$CH_3$ or —$(CHOH)_2$—$CH_2OH$, $R_2$ and $R_3$ are not the same and represent either hydrogen or the group —$(CH_2)_3CONH(CH_2)_4$—NH—$R_4$, wherein $R_4$ represents hydrogen or a usual label group for immunoassays or usual coating/support materials for solid phase immunoassays or immunogenic groups for the preparation of antibodies.

Examples of the "usual label groups" are radioactive labels, enzyme labels, fluorescence labels or chemiluminescence labels.

Examples of "support materials" for solid phase immunoassays are microtiter plates, polystyrene tubes or beads, to which the "usual coating materials" are bound covalently or by absorption. Examples of the "usual coating materials" are proteins, such as serum albumins, transferrin, immunoglobulins, or synthetic polypeptides, e.g. poly (phenylalanine-lysine), etc. However, compounds I ($R_4$=H) could also be bound covalently to the appropriate solid support materials, e.g. carboxy group-containing plastic surfaces.

Proteins and peptides with high immunogenicity, such as keyhole limpet hemocyanine, thyroglobulin or polyacrylamides are examples of "immunogenic groups".

The specified pterin derivatives I may be prepared by reacting pterin derivatives having the general formula II $$R_5\underset{R_6-HN}{\overset{}{\underset{N}{\|}}}\overset{O}{\underset{N}{\|}}\overset{}{\underset{N}{\|}}\overset{N}{\underset{}{\|}}R_1 \quad\quad II$$

wherein $R_1$ is as defined above and $R_5$ and $R_6$ are not the same and represent either hydrogen or the group —$(CH_2)_3COOH$ with 1,4-diaminobutane, if desired followed by linking the terminal free amino group with a label, a coating/support material, or an immunogenic group using known reactions.

The present invention relates to the use of said pterin derivatives for the preparation of immunoassays for the determination of neopterin or biopterin.

The pterin derivatives having the general formula II that are used as the starting materials for the preparation of the pterin derivatives I can be prepared in the following way:

Neopterin or biopterin are reacted with 4-bromobutyric acid ethyl ester to form $N^3$-(3-carboxypropyl)-neopterin or —biopterin ethyl ester. This ethyl ester may be hydrolyzed with acid to form the $N^3$-carboxypropyl pterin derivative; however, hydrolyzing the ester under alkaline condition yields with simultaneous rearrangement the $N^2$-carboxypropyl pterin derivative, with the substituent at the 2-amino group. Both these carboxylic acid derivatives may be further reacted with 1,4-diaminobutane employing the usual activation reactions of the carboxylic group, e.g. it may be carried out in anhydrous dimethylformamide using N-hydroxysuccinimide with the addition of morpholinoethyl isonitrile and lutidine, or with carbodiimides as activating agents, yielding the ω-aminobutylamides of the above 3-carboxypropyl pterin derivatives. It is also possible to rearrange the $N^3$-amide by means of alkali to the corresponding $N^2$-derivative.

Substances wherein $R_4$ is a label group, a coating/support material or an immunogenic group are prepared from substances having the general formula I wherein $R_4$ represents hydrogen by a reaction with the appropriate label groups, a coating/support material for solid phase immunoassays, or an immunogenic group.

The substances of the general formula I wherein $R_4$ represents hydrogen can also be utilized for producing antibodies against neopterin and biopterin. For this, they are attached to the immunogenic groups commonly used for this purpose such as immunogenic proteins, more particularly bovine serum albumin (BSA), thyroglobulin, keyhole limpet hemocyanine or polyacrylamides, etc. The usual adjuvants may be used for immunisations in rabbits, sheep, chicken or mice. Numbers and intervals of the booster injections may be varied according to the respective animal species. Moreover, antibodies generated by means of other substances against biopterin and neopterin have shown to be potentially suitable for preparing corresponding immunoassays. It is also possible to use monoclonal antibodies produced, for example, from the spleen cells of immunized mice according to the usual procedures.

The derivatives described in formula I, bound to the appropriate coating or support materials, e.g. BSA, immunoglobulins, transferrin or plastic surfaces may also be employed in immunoassays according to the method of EP-0 135 071.

Suitable radioactive labels are, for example, 3'-$^{125}$iodotyrosyl or 4'-hydroxy-3'-$^{125}$iodophenylpropionic acid derivatives having the formulae

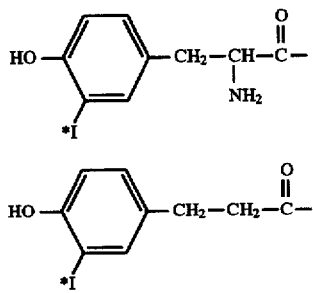

which are obtained via "indirect labelling" by reacting the ω-aminoneopterin derivatives (or the ω-aminobiopterin derivatives) I A/B with the activated N-hydroxysuccinimide ester of the appropriate radioactive label compound (see formulae above) and subsequent separation of the resulting product by HPLC. Alternatively, these compounds can be "directly radiolabelled" by first preparing the analogous iodine-free compound, which is finally labelled, e.g. by the usual chloramine T method using radioactive iodide.

Suitable enzyme labels are, for example, alkaline phosphatase, horse-raddish peroxidase or β-galactosidase which are activated with the usual methods (e.g. with glutaraldehyde, epoxy derivatives or by periodate oxidation) and are coupled to the terminal amino group of the ω-aminopterin derivatives. Purification is effected by gel chromatography methods, usually by HPLC.

A suitable fluorescence label is, for example, the fluorescein group which is readily introduced by reacting the ω-aminopterin derivatives with fluorescein isothiocyanate. The compounds are purified by means of HPLC.

Suitable chemiluminescence labels are, for example, acridinium esters, luminol derivatives or ABEI (N-(4-aminobutyl)-N-ethylisoluminol), which are usually introduced via commercially available activated derivatives; the products are purified by HPLC.

The following Examples illustrate in detail the preparation of the starting materials (formula II) as well as of the substances according to the invention (formula I) and the use thereof, not necessarily giving all possibilities.

The laboratory chemicals used were of high purity quality from E. Merck (Darmstadt), Fluka (Neu-Ulm), Sigma (München), or Calbiochem (Bad Soden); neopterin and biopterin were from Dr. Schircks Laboratories (Jona, Switzerland), other speciality materials as given in the appropriate examples. Cellulose sheets for thin layer chromatography were from Schleicher and Schüll (Dassel).

Preparation of Intermediates of the Formula II $N^2$-(3-carboxypropyl)-neopterin ethyl ester (II A)

Twelve milligrams of neopterin are suspended in 1.5 ml of dimethylformamide (DMF); after addition of 14 μ4-bromobutyric acid ethyl ester and 26 mg of anhydrous $K_2CO_3$, mixture is shaken at room temperature for 2 days. Preparative thin layer chromatography {cellulose sheets; n-propanol/3% aqueous $NH_3$ (2/1)}was carried out using an aliquot of the reaction mixture. The main band ($R_f$ about 0.65) is eluted with methanol-water.

Alternatively, the product may be isolated by preparative HPLC on a column of Deltapak C-18 (Millipore, Eschborn) with gradient elution (eluent A: 0.1% aqueous trifluoroacetic acid, eluent B: 0.1% trifluoroacetic acid in acetonitrile) 0–25% B in 30 min. Retention time about 21 min. Yield 32%.

$N^3$-(3-carboxypropyl)-neopterin (II B)

Five milligrams of the above ethyl ester are gently shaken in 2 ml of water with 500 μl of 1N hydrochloric acid for 2 days, protected from light; the ester is then completely hydrolyzed. The mixture is taken to dryness under high vacuum in a rotary evaporator. Yield 3.7 mg (80%). The $R_f$ value is about 0.23 {cellulose sheets; n-propanol/3% aqueous $NH_3$ (2/1)}.

$N^2$-(3-carboxypropyl)-neopterin (II C)

Five milligrams of $N^3$-(3-carboxypropyl)-neopterin ethyl ester are treated with 2 ml of 0.2 N sodium hydroxide solution at room temperature with light-protection; the mixture is then neutralized with hydrochloric acid. Thin layer chromatography {cellulose sheets; n-propanol/3% aqueous $NH_3$(2/1)}provides an $R_f$ value of 0.15. The yield is 3.2 mg (69%).

Preparation of the Substances of the Formula I

EXAMPLE 1

$N^3$-(ω-aminobutyl-3-carboxamido-propyl)-neopterin I A ("$N^3$-ω-aminoneopterin")

Three milligrams of $N^3$-(3-carboxypropyl)-neopterin II B are dissolved in 1.5 ml of DMF (anhydrous) and mixed with 5 mg of N-hydroxysuccinimide and 6 μl of morpholinoethyl isonitrile in 50 μl of DMF (anhydrous) and 4 μl of lutidine. After three days of gentle shaking at room temperature with light-protection, 50 μl of 1,4-diaminobutane are added, and shaking of the mixture is continued for 2 more days. An aliquot is purified by preparative thin layer chromatography {cellulose sheets; n-propanol/3% aqueous $NH_3$ (2.5/1)}. The main band ($R_f$ about 0.3) is eluted with methanol-water and evaporated in a rotary evaporator.

The same product is obtained in the following way: 8.5 mg of $N^3$-(3-carboxypropyl)-neopterin ethyl ester II A are treated with 6 ml of 1N hydrochloric acid for 2 days at room temperature with light-protection. The mixture is taken to dryness in a rotary evaporator under high vacuum. After repeating this three times with 2 ml of water, the residue is dissolved in 2 ml of dry DMF and 12 mg of ethyl carbodiimide are added. After shaking for 16 hours at room temperature with light-protection, 15 µl of 1,4-diaminobutane are added and shaking is continued for another day. The mixture is taken again to dryness in a rotary evaporator under high vacuum, this is being repeated with DMF. The purification is analogous to above, $R_f$ 0.32.

EXAMPLE 2

$N^2$-(ω-aminobutyl-3-carboxamido-propyl)-neopterin I B ("$N^2$-ω-aminoneopterin")

Seven milligrams of $N^2$-(3-carboxypropyl)-neopterin II C are dissolved in 2 ml of DMF (anhydrous) and 5 µl of lutidine. 6 mg of N-hydroxysuccinimide and 7 µl of morpholinoethyl isonitrile are dissolved in 120 µl of DMF (anhydrous) and added to the above solution. The mixture is stirred at room temperature with light-protection for 5 days. Then 100 µl of 1,4-diaminobutane are added and the mixture is gently shaken for another 16 hours. Preparative thin layer chromatography on cellulose sheets with n-propanol/3% aqueous $NH_3$(2.5/1) as the mobile phase gives a main band with $R_f$ about 0.27. It is eluted with methanol/water/ ammonia and taken to dryness in a rotary evaporator. Yield 4.3 mg (53%).

This substance is also obtained in the following way:
One milligram of the $N^3$-ω-aminoneopterin derivative I A (obtained according to Example 1) is gently shaken in 500 µl of 0.2N NaOH with light-protection at room temperature for 4 hours. The resulting mixture is neutralized with hydrochloric acid and lyophilized. Thin layer chromatography on cellulose sheets with n-propanol/3% aqueous $NH_3$(2.5/1) as mobile phase gives an $R_f$ of about 0.27.

EXAMPLE 3

"$N^3$-neopterin-alkaline phosphatase label"

0.24 mg of the $N^3$-ω-aminoneopterin derivative I A according to Example 1 in 25 µl of carbonate buffer (1M, pH 9) are mixed at 4° C. with 55 µl (0.5 mg) of activated alkaline phosphatase (Pierce Europe, Netherlands) and allowed to stand overnight at 4° C. Then, 15 µl of lysine (2M) are added, followed 2 h later by 175 µl of bovine serum albumin (BSA; 1% aq.). The mixture is separated by gel chromatography (NAP-10 column; Pharmacia, Freiburg).

EXAMPLE 4

"$N^2$-neopterin-alkaline phosphatase label"

In the same manner as described in Example 3, 0.24 mg of the $N^2$-ω-aminoneopterin derivative I B (cf. Example 2) are treated with alkaline phosphatase (preactivated; Pierce Europe); the product is separated by gel chromatography (NAP-10) as above.

EXAMPLE 5

"$N^2$-neopterin-BSA-conjugate"

To twenty milligrams of bovine serum albumin (BSA; Bayer, Leverkusen) in 2 ml of water are added at 4° C. 100 µl of glutaraldehyde. After 1 hour at room temperature, 0.5 mg of the $N^3$-ω-aminoneopterin derivative I A (according to Example 1) in 1 ml of methanol/water are added. Excess aldehyde groups are saturated with lysine. The product is dialyzed against water (5 liters in total) and lyophilized in aliquots. Yield 14 mg.

EXAMPLE 6

"$N^3$-neopterin-KLH conjugate"

In the same manner as described in Example 5, 25 mg of keyhole limpet hemocyanin (KLH; Calbiochem, Bad Soden) in 2 ml of water are reacted with $N^3$-ω-aminoneopterin derivative I A. The product is dialyzed against 6 liters of water in total (several changes) and lyophilized in aliquots. Yield 18 mg.

EXAMPLE 7

"$N^2$-neopterin-BSA conjugate"

In the same manner as described in Example 5, 20 mg of BSA are reacted with the $N^2$-ω-aminoneopterin derivative I B, and the resulting product is dialyzed. Yield 13 mg.

EXAMPLE 8

"$N^3$-neopterin-fluorescein-label"

0.4 mg of the ω-aminoneopterin derivative I A are dissolved in 1 ml of 0.05M borate buffer pH 8.2, then 40 µl of a solution of fluorescein isothiocyanate (10 mg/ml in dimethyl sulfoxide) are added. The same amount is added after 14 hours at room temperature with light-protection. After further 18 hours, the mixture is separated by HPLC (Eurospher 80-C18, gradient elution as in example 1, 0–25% B in 45 min, 25–100% B in 10 min); retention time 52 min.

EXAMPLE 9

"$N^2$-neopterin-acridinium ester chemiluminescence label"

Ten microliters of the ω-aminoneopterin derivative I A according to Example 2 (0.6 mg/ml) are added to 50 µl of a sodium phosphate buffer (50 mM, pH 8.5); then 40 µl of an acridinium ester solution (MA70, 1 mg/ml; Hoechst Behring, Frankfurt) are added and the mixture is incubated at room temperature with light-protection for 15 minutes. The labelled neopterin is purified via C18-reverse phase HPLC by a gradient of eluent A (water/acetonitrile, 95/5) and eluent B (acetonitrile/water, 90/10), both containing trifluoroacetic acid, 0.1%.

EXAMPLE 10

Enzyme Immunoassay for the Determination of Neopterin in Body Fluids

Preparation of the Tracer

The neopterin/alkaline phosphatase conjugate according to Example 5 is diluted in a buffer comprising 100 mM Hepes pH 6.4, 1 mM $MgCl_2$, 80 mg/l food dye Blue, 10.7 g/l alkaline phosphatase (1 U/mg), 1.07 g/l of each sheep and bovine IgG and 16 g/l of BSA to about 1,800 U/µi, divided into 2.5 ml aliquots and lyophilized.

Preparation of Coated Microtiter Plates

To each well of microtiter plates (Maxisorp F96, Nunc) are added 300 µl of a solution of 10 mg/l of donkey-anti-sheep antibody in 10 mM tris/HCl (pH 7.8, 10 mM NaCl). After standing overnight, the solution is removed by suction, and the plates are saturated with 0.5% BSA/2% sugar solution for 2 hours. 300 μl of an anti-neopterin antiserum dilution 2 mg/l) in 10 mM tris/HCl (pH 7.8, 10 mM NaCl) are added per well. After 18 to 24 hours the solution is removed by suction, and the plates are again saturated as above and then dried by lyophilisation.

Preparation of the Standards

Neopterin-free human serum is sterile filtered, then 0.05% of sodium azide and the desired amount of neopterin are added.

Assay Procedure

1. Reconstitute 2.5 ml of the lyophilized tracer with 40 ml of 100 mM Hepes buffer (pH 6.5, 150 mM $MgCl_2$).
2. Pipette 50 μl of standard or patient's serum (or plasma) and 150 μl of tracer into the wells of an uncoated microtiter plate and thoroughly mix.
3. Transfer 150 μl of the resulting mixture into the antibody-coated microtiter plate and incubate at room temperature with light-protection for 2 hours.
4. Wash three times.
5. Pipette 10 μl of 4-nitrophenyl phosphate (4-NPP-solution) per well and incubate for 30 minutes.
6. Stop the reaction by the addition of 10 μl of 2 N sodium hydroxide per well.
7. Measure the optical densities (OD) in a photometer at a wavelength of 405 nm.

Result

| Typical Standard Values | |
|---|---|
| Concentration nmol/l | OD |
| 2 | 1.978 |
| 5 | 1.477 |
| 10 | 1.098 |
| 25 | 0.706 |
| 50 | 0.530 |

| Correctness of Dilution (Dilution with zero serum, average of 6 patients' sera) | |
|---|---|
| | Recovery % |
| Original | 111 |
| 1:2 | 102 |
| 1:4 | 100 |
| 1:8 | 98 |
| 1:16 | 104 |

| Recovery of Standard 5 (50 nmol/l) (Average of 10 sera) | |
|---|---|
| 1 + 1 | 94% |
| 1 + 2 | 94% |

| Intra assay precision n = 10 | | Inter assay precision n = 10 | |
|---|---|---|---|
| Concentration nmoles/l | CV % | Concentration nmoles/l | CV % |
| 3.0 | 6.6 | 2.8 | 13.8 |
| 5.5 | 5.6 | 4.2 | 9.8 |
| 12.6 | 3.0 | 6.5 | 7.4 |
| 29.9 | 3.7 | 10.6 | 8.1 |
| 32.2 | 4.8 | 19.3 | 6.8 |
| 45.4 | 6.2 | 29.8 | 5.3 |

Lower limit of detection: 2 nmol/l

EXAMPLE 11

Chemiluminescence Immunoassay for the determination of neopterin in body fluids

Preparation of the Tracer

The labelled neopterin according to Example 9 is diluted in a buffer comprising 50 mM K phosphate pH 6.5, 20 g/l BSA, 0.8 g/l of each sheep and mouse IgG, 0.2 g/l of food dye Blue and 0.1 g/l Kathon CG to about 1,800 RLU/μl, divided into 1.4 ml aliquots and lyophilized.

Preparation of the Standards

Neopterin-free human serum is sterile filtered, then 0.05% of sodium azide and the desired amount of neopterin are added.

Preparation of Coated Tubes

An anti-neopterin antiserum is diluted in 10 mM tris/HCl (pH 7.8, 10 mM NaCl) to 6.6 mg/l, then pipetted into Star tubes (Maxisorp, Nunc), 300 μl per tube, and incubated for 18 to 24 hours at room temperature. Then the solution is removed by suction, and the tubes are saturated with a solution of sugar/BSA (2%/0.3%). After 2 hours at room temperature the solution is again removed by suction, and the tubes are lyophilized.

Assay Procedure

1. Reconstitute 1.4 ml of the tracer lyophilizate with 20 ml of 50 mMK phosphate buffer pH 6.5.
2. Pipette 50 μl of standard or patient's sample and 250 μl of tracer into a tube coated with anti-neopterin-antibody.
3. Incubate with shaking at 30 rpm and room temperature with light-protection for 2 hours.
4. Wash the tubes four times.
5. Measure in a luminometer.

Result

| Typical Standard Values | |
|---|---|
| Concentration nmol/l | RLU |
| 2 | 49,587 |
| 5 | 34,589 |
| 15 | 14,389 |
| 50 | 5,137 |
| 150 | 1,964 |
| 500 | 935 |

| Correctness of Dilution (Dilution with zero serum, average of 10 sera) ||
|---|---|
| Dilution | Recovery % |
| Original | 108 |
| 1:2 | 102 |
| 1:4 | 94 |
| 1:8 | 100 |
| 1:16 | 98 |
| 1:32 | 111 |

| Recovery {Sera with added Standard 6 (500 nmol/l)} ||
|---|---|
| 2 + 1 | 103% |
| 1 + 1 | 98% |
| 1 + 2 | 108% |

| Precision ||||
|---|---|---|---|
| Intra assay precision n = 10 || Inter assay precision n = 10 ||
| Concentration nmoles/l | CV % | Concentration nmoles/l | CV % |
| 3.2 | 7.0 | 2.5 | 13 |
| 6.5 | 4.8 | 5.3 | 7.2 |
| 11.0 | 3.3 | 15.0 | 6.6 |
| 25.4 | 3.1 | 35.0 | 5.7 |
| 39.7 | 4.1 | 44.0 | 6.3 |
| 73.0 | 6.2 | 89.0 | 8.9 |
| 238.0 | 9.3 | 175.0 | 12.8 |
| Lower limit of detection: 2 nmol/l ||||

I claim:

1. Pterin derivative having the general formula I

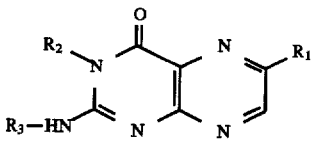

wherein $R_1$ is —(CHOH)$_2$—CH$_3$ or —(CHOH)$_2$—CH$_2$OH, and one of $R_2$ and $R_3$ is hydrogen and the other is a linker of formula —(CH$_2$)$_3$CONH(CH$_2$)$_4$—NH—R$_4$, wherein $R_4$ is an immunoassay label, a coated or uncoated support for solid phase immunoassays, or an immunogenic group.

2. Pterin derivative according to claim 1, wherein $R_3$ is an immunoassay label selected from the group consisting of radioactive labels, enzyme labels, fluorescent labels, and chemiluminescent labels.

3. In a method of using a pterin derivative for the preparation of an immunoassay reagent for the determination of neopterin or biopterin, the improvement wherein the pterin derivative is the pterin derivative of claim 1.

4. A process for preparing a pterin derivative having the general formula I

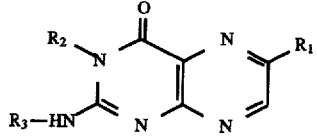

wherein $R_1$ is —(CHOH)$_2$—CH$_3$ or —(CHOH)$_2$—CH$_2$OH, and one of $R_2$ and $R_3$ is hydrogen and the other is a linker of formula —(CH$_2$)$_3$CONH(CH$_2$)$_4$—NH—R$_4$, wherein $R_4$ is hydrogen or is an immunoassay label, a coated or uncoated support for solid phase immunoassays, or an immunogenic group for the preparation of antibodies, comprising the steps of:

(a) reacting (i) a pterin derivative having the general formula II

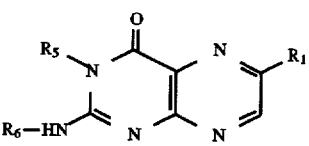

wherein $R_1$ is as defined above and one of $R_5$ and $R_6$ is hydrogen and the other is —(CH$_2$)$_3$COOH, with (ii) 1,4-diaminobutane, followed, optionally, by (b) reacting the terminal amino group of the linker with an immunoassay label, a coated or uncoated support for solid phase immunoassays, or an immunogenic group.

5. Pterin derivative having the general formula I

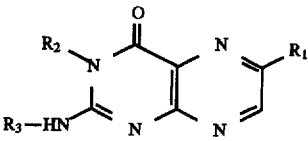

wherein $R_1$ is —(CHOH)$_2$—CH$_3$ or —(CHOH)$_2$—CH$_2$OH, and one of $R_2$ and $R_3$ is hydrogen and the other is a linker of formula —(CH$_2$)$_3$CONH(CH$_2$)$_4$—NH—R$_4$, wherein $R_4$ is hydrogen.

* * * * *